(12) United States Patent
Parker, Jr.

(10) Patent No.: US 7,537,893 B2
(45) Date of Patent: May 26, 2009

(54) MITOCHONDRIAL ND5 GENE MUTATIONS IN PARKINSON'S DISEASE

(75) Inventor: W. Davis Parker, Jr., Charlottesville, VA (US)

(73) Assignee: Gene Solutions, LLC, Charlottesville, VA (US)

( * ) Notice: Subject to any disclaimer, the term of this patent is extended or adjusted under 35 U.S.C. 154(b) by 87 days.

(21) Appl. No.: 11/363,531

(22) Filed: Feb. 27, 2006

(65) Prior Publication Data

US 2006/0194239 A1 Aug. 31, 2006

Related U.S. Application Data

(60) Provisional application No. 60/656,223, filed on Feb. 25, 2005.

(51) Int. Cl.
*C12Q 1/68* (2006.01)
*C07H 21/02* (2006.01)
*C07H 21/04* (2006.01)
*G01N 33/53* (2006.01)
*C07K 14/435* (2006.01)

(52) U.S. Cl. .......... 435/6; 536/23.1; 536/23.5; 536/24.31; 435/7.1; 530/350

(58) Field of Classification Search .............. None
See application file for complete search history.

(56) References Cited

OTHER PUBLICATIONS

Parker et al. Biochemical and Biophysical Research Communications. 326 (Dec. 7, 2004): 667-669.*
Smigrodzki et al. Neurobiology of Aging. Nov.-Dec. 2004.25: 1273-1281.*
Schoeler et al. Clinical Neuropathology. 2007.26: 164-168.*
Hirschhorn et al. Genetics in Medicine. vol. 4, No. 2, pp. 45-61, Mar. 2002.*
Huerta et al. Journal of Neurological Sciences. 2005. 236: 49-54.*
Kosel et al. Neurogenetics. 1998. 1: 197-204.*

* cited by examiner

*Primary Examiner*—Carla Myers
(74) *Attorney, Agent, or Firm*—Wolf, Greenfield & Sacks, P.C.

(57) ABSTRACT

The present invention provides methods for diagnosing and treating Parkinson's disease based on mitochondrial mutations. The present invention also provides methods for diagnosing and treating other diseases and disorders based on mitochondrial mutations.

8 Claims, No Drawings

SEQUENCE LISTING

<160> NUMBER OF SEQ ID NOS: 26

<210> SEQ ID NO 1
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 1
ccgtacaacc ctaacataac ca                                             22

<210> SEQ ID NO 2
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 2
gtgttccaat gtctttgtgg tt                                             22

<210> SEQ ID NO 3
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 3
tctcagccct cctaatgacc tc                                             22

<210> SEQ ID NO 4
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 4
tctatgtagc cgttgagttg tg                                            22

<210> SEQ ID NO 5
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 5
caacaccctc ctagccctac tac                                           23

<210> SEQ ID NO 6
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 6
gagtcaggta gttagtatta ggag                                          24

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
ctgttcccca accttttcct                                               20

<210> SEQ ID NO 8
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 8
cgaggttagc gaggcttg                                                 18

<210> SEQ ID NO 9
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 9
gcactcacag tcgcatcata at                                            22

<210> SEQ ID NO 10
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 10
ctgattaatg tttgggtctg ag                                            22

<210> SEQ ID NO 11

```
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 11
ccctgtagca ttgttcgtt                                              19

<210> SEQ ID NO 12
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 12
gctcaggcgt ttgtgtatg                                              19

<210> SEQ ID NO 13
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 13
caggaatacc tttcctcaca gg                                          22

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
gaggagtagg ggcaggtttt                                             20

<210> SEQ ID NO 15
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 15
aaatccccac tatgcacatt tt                                          22

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
gggtggtggt tgtggtaaac                                             20

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
```

-continued ccccgagcaa tctcaattac                                              20

<210> SEQ ID NO 18
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 18
tctaagcctt ctcctattta tgg                                          23

<210> SEQ ID NO 19
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 19
ccgctaacaa tcaatactaa acc                                          23

<210> SEQ ID NO 20
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 20
gtataattgt ctgggtcgcc ta                                           22

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 21
tccgagcagt acatgctaag                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 22
atgccattgc gattagaatg                                              20

<210> SEQ ID NO 23
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 23
caacctccta ctcctcattg tac                                          23

<210> SEQ ID NO 24
<211> LENGTH: 22
<212> TYPE: DNA

-continued

```
<213> ORGANISM: Artificial Sequence
<220> FEATURE:
<223> OTHER INFORMATION: Synthetic Oligonucleotide

<400> SEQUENCE: 24
gtaatgggta tggagacata tc                                             22

<210> SEQ ID NO 25
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 25
aacttcctac cactcaccct ag                                             22

<210> SEQ ID NO 26
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 26
gtaggaatgc ggtagtagtt ag                                             22
```

MITOCHONDRIAL ND5 GENE MUTATIONS IN PARKINSON'S DISEASE

RELATED APPLICATIONS

This application claims priority under 35 U.S.C. §119 from U.S. provisional application Ser. No. 60/656,223, filed Feb. 25, 2005, the entire content of which is incorporated herein in its entirety.

US Government Rights

This invention was made with United States Government support under Grant No. RO1 NS039788, awarded by the National Institutes of Health. The United States Government may have certain rights in the invention.

FIELD OF THE INVENTION

The present invention is directed to methods of measuring mitochondrial complex I mutations in Parkinson's Disease and Aging, and to methods of diagnosing Parkinson's Diseases and other diseases.

BACKGROUND OF THE INVENTION

Parkinson's disease (PD) is a progressive neurological disorder of late-middle and old age. Although PD is rarely inherited through autosomal or matrilineal maternal pathways, it most often occurs sporadically without identifiable familial patterns (Simon et al., *Neurology* 54 (2000) 703). Pathologically, PD involves the loss of a number of neural populations, such as the serotonergic neurons in raphe nuclei, the dopaminergic neurons in substantia nigra and the ventral tegmental area, cholinergic neurons of the basal forebrain, and the noradrenergic neurons in the locus ceruleus.

Idiopathic Parkinson's disease (PD) involves a systemic loss of activity of complex I of the mitochondrial electron transport chain, the target enzyme of the parkinsonism-producing neurotoxin, MPTP. This biochemical lesion plays a key pathogenic role. Transfer of PD mitochondrial DNA to a non-PD cell recapitulates this loss of activity and several other pathogenic features of PD, suggesting that this lesion may arise, at least in part, from mitochondrial DNA.

Many human disorders including idiopathic Parkinson's disease (PD) typically arise without clear patterns of inheritance. The lack of recognizable familial associations has led to consideration of non-genetic factors such as toxins or infectious agents as potential causes. In 1989, heteroplasmic mitochondrial DNA (mtDNA) mutations was proposed as a general genetic model that might explain some idiopathic illnesses (Parker et al., *Ann. Neurol.* 26 (1989) 719; Parker, In: *R. M Pascuzzi, Editors, New Developments in Neuromuscular Disease*, Indiana University Printing Services, Bloomington, Ind. (1990) 59; Parker and Swerdlow, *J. Clin. Ligand Assay Soc.* 23 (2000) 141; Parker and Swerdlow, *Am. J. Hum. Genet.* 66 (1998) 758). This model predicts that a disorder arising through this genetic mechanism should manifest an electron transport chain (ETC) defect of some sort because all mitochondrial gene products are components of the ETC. This model also predicts that the biochemical lesion is likely to be anatomically generalized because of the universal distribution of the mitochondrial genes. Platelet mitochondria in patients with idiopathic PD were studied and a substantial and specific loss of complex I activity was found. A similar lesion in the substantia nigra in idiopathic PD has been reported.

Loss of complex I activity (NADH:ubiquinone oxidoreductase) probably contributes to the cell loss and dysfunction seen in PD as evidenced by the fact that inhibition of this enzyme causes PD in humans and animal. Activity of this critical redox enzyme is depressed in multiple tissues in PD including platelets, muscle, non-nigral brain, as well as substantia nigra, the conventional focus of PD research. A few studies that relied on assay of tissue homogenates rather than purified mitochondria failed to identify this defect indicating the extreme importance of methodological factors (e.g. Nuerta et al., *J. Neurol. Sci.* 236 (2005) 49; Simon et al., *Neurobiol. Aging,* 1 (2004) 71).

This loss of complex I activity arises at least in part from mitochondrial DNA (mtDNA) as demonstrated by studies on cytoplasmic hybrids (cybrids). Cybrids are created by the transfer of either control or PD mitochondria (and their mtDNA) into culturable cells depleted of their own endogenous mtDNA. PD cybrids demonstrate loss of complex I activity and a tendency toward apoptotic cell death as well as other features of PD, such as increased free oxygen radical production, altered calcium homeostasis, increased antioxidant enzymes, inclusion bodies containing synuclein, and fully formed Lewy bodies, the histopathological hallmark of PD. These studies strongly suggest that PD mtDNA encodes pathogenic information and raises the possibility of the presence of pathogenic mtDNA mutations in PD.

A number of studies detected homoplasmic and high-frequency heteroplasmic mtDNA mutations in PD, including deletions and single-nucleotide substitutions, but no solid correlations with the PD phenotype have been found (Mellick et al., *J. Neural Trans.* 111 (2004) 191; Garcia-Lozano et al., *Eur. Neurol.* 48 (2002) 34). These studies did not detect low frequency heteroplasmic mutations.

Studies relying on direct sequencing of PCR-amplified mtDNA lack the ability to detect low frequency, heteroplasmic mutations. Detection of such low-abundance mtDNA mutations requires sequencing numerous independent clones of the relevant genes. These mutations may be important since the phenotypic effects of mtDNA mutations in other mitochondrial diseases can manifest at low levels of heteroplasmy. Simon et al. recently conducted a study employing a cloning strategy and found a background of mtDNA mutations in PD and aged controls but failed to correlate any specific mutation with the phenotype (Simon et al., *Genomics* 73 (2001) 113).

Cybrid studies implicated mitochondrial DNA in the pathogenesis of idiopathic PD but numerous studies of mtDNA sequence failed to identify mutations strongly associated with PD. The studies, however, may not have been carried out in enough depth to identify low frequency heteroplasmic mutations.

All seven complex I genes from brain tissue of idiopathic PD and controls have been sequenced by Applicant in previously unattained depth. PD brains did not contain significantly more mutations than control brain. However, the data presented here suggest that a small region of the mitochondrial ND5 gene from codon 120 to codon 150 harbors mutations segregating PD from control. A less important region was identified in ND2.

Applicant demonstrated the predictive potential of the identified correlation by sequencing this region of ND5 from 8 PD and 8 control brain samples. The presence or absence of heteroplasmic mutations correctly classified 15 out of 16 brain samples.

There is a long felt need in the art for methods of diagnosing and treating Parkinson's Disease, and other diseases and disorders, based on gene mutations. The present invention satisfies these needs.

SUMMARY OF THE INVENTION

The present invention is directed to correlating mitochondrial DNA mutations with diseases and disorders. The present invention is also directed to methods of diagnosing and treating diseases and disorders based on mitochondrial DNA mutations. In one aspect, the disease is Parkinson's Disease. In another aspect, the disease or disorder is aging.

The present disclosure provides extensive clonal sequencing of the seven mitochondrial genes encoding complex I subunits in PD and age-matched control frontal cortex. Each gene was completely sequenced an average of 94.4 times for each subject. Amino acid-changing mutations were found at the frequency of 59.3 per million bases in both PD and controls, corresponding to approximately 32% of the mitochondrial genomes in the average sample having at least one mutation in a complex I gene. Individual low frequency mutations had an abundance of 1-10%. Significant inter-individual variation in mutation frequency was observed. Several amino acid-changing mutations were identified and multiple PD brains but not in controls. Analysis of the data revealed areas in ND genes with a higher mutation frequency in PD that allowed differentiation of PD from controls. Total mutational burden due to low-abundance heteroplasmy is high and may play a role in human disease.

Example 2 describes the prospectively evaluated low frequency, amino acid changing, heteroplasmic mutations in a narrow region of ND5, a mitochondrial gene encoding a complex I subunit, in brain tissue from PD and controls. The presence or absence of amino acid changing mutations correctly classified 15 of 16 samples. Heteroplasmic mutations in a specific region of ND5 largely segregate PD from controls and may be of major pathogenic importance in idiopathic PD.

In one aspect, the invention provides methods of diagnosing diseases and disorders based on mitochondrial nucleic acid mutations. In another aspect, the invention provides methods of diagnosing diseases and disorders based on mutations of protein sequences encoded by mitochondrial nucleic acid sequences. Methods for detecting and measuring mutations in nucleic acid sequences and mutations in amino acid sequences are described herein, or are known to those of ordinary skill in the art.

Various aspects and embodiments of the invention are described in further detail below.

DETAILED DESCRIPTION OF THE INVENTION

Definitions

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the term "antibody" refers to a polyclonal or monoclonal antibody or a binding fragment thereof such as Fab, F(ab')2 and Fv fragments.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A."

A "coding region" of a gene consists of the nucleotide residues of the coding strand of the gene and the nucleotide residues of the non-coding strand of the gene which are homologous with or complementary to, respectively, an mRNA molecule which is produced by transcription of the gene. It is understood that, owing to mRNA processing which occurs in certain instances in eukaryotic cells, the mRNA-coding region of a gene may comprise a single region or a plurality of regions separated from one another in the gene as it occurs in the genome. Where the mRNA-coding region of a gene comprises separate regions in a genome, "mRNA-coding region" refers both individually and collectively to each of these regions.

A "coding region" of an mRNA molecule consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g. amino acid residues in a protein export signal sequence).

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is anti-parallel to the first region if the residue is thymine or uracil.

Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion. For example, two nucleic acids are complementary to each other when a substantial number (at least 50%) of corresponding positions in each of the molecules are occupied by nucleotides which normally base pair with each other (e.g., A:T and G:C nucleotide pairs).

The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence polarization or altered light scattering.

A "disease" is a state of health of an animal wherein the animal cannot maintain homeostasis, and wherein if the disease is not ameliorated then the animal's health continues to deteriorate. The term "disease state" is intended to encompass any condition that is associated with an impairment of the normal state of a living animal or plant including congenital defects, pathological conditions such as cancer, and responses to environmental factors and infectious agents (bacterial, viral, etc.). In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, are reduced.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, a "functional" biological molecule is a biological molecule in a form in which it exhibits a property by which it is characterized. A functional enzyme, for example, is one which exhibits the characteristic catalytic activity by which the enzyme is characterized. The terms "functional" and "active" are used interchangeably herein.

The terms "growth" and "replication" are used interchangeably herein.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator "http://www.ncbi.nlm.nih.gov/BLAST/". BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See http://www.ncbi.nlm.nih.gov.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

"Operably linked" refers to a juxtaposition wherein the components are configured so as to perform their usual function. Thus, control sequences or promoters operably linked to a coding sequence are capable of effecting the expression of the coding sequence. By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, the term "parenteral" includes administration subcutaneously, intravenously or intramuscularly.

The term "peptide" encompasses a sequence of 3 or more amino acids wherein the amino acids are naturally occurring or synthetic (non-naturally occurring) amino acids and typically refers to short polypeptides.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

A "polynucleotide" means a single strand or parallel and anti-parallel strands of a nucleic acid. Thus, a polynucleotide may be either a single-stranded or a double-stranded nucleic acid. A "portion" of a polynucleotide means at least at least about twenty sequential nucleotide residues of the polynucleotide. It is understood that a portion of a polynucleotide may include every nucleotide residue of the polynucleotide.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

Conventional notation is used herein to portray polypeptide sequences: the left-hand end of a polypeptide sequence is the amino-terminus; the right-hand end of a polypeptide sequence is the carboxyl-terminus.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive promoter" is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

"Therapeutic agent," "pharmaceutical agent" or "drug" refers to any therapeutic or prophylactic agent which may be used in the treatment (including the prevention, diagnosis, alleviation, or cure) of a malady, affliction, disease or injury in a patient.

As used herein, the term "treating" includes alleviating the symptoms associated with a specific disorder or condition and/or preventing or eliminating said symptoms. For example, treating cancer includes preventing or slowing the growth and/or division of cancer cells as well as killing cancer cells.

A "subject" of diagnosis or treatment is a mammal, including a human.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

Used interchangeably herein are the following pairs of words (1) "detect" and "identify"; (2) "select" and "isolate"; and (3) "sperm surface" and "sperm plasma membrane."

The phrase "under transcriptional control" or "operatively linked" as used herein means that the promoter is in the correct location and orientation in relation to the polynucleotides to control RNA polymerase initiation and expression of the polynucleotides.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

DETAILED DESCRIPTION

Example 1 shows that a small region in ND5 and to a lesser extent a small region in ND2 harbor mutations segregating PD from controls. Example 2 shows that the observation can be used to classify a brain sample as PD or control. In addition, example 2 shows that mutation data obtained from blood can also classify a sample as PD. Both studies identified relevant heteroplasmic mutations but at frequencies well below that previously associated with disease causing mutations. The studies necessarily average across millions of cells and it may be the case that mutation frequency in some individual cells may be much higher. The fact that PD brain does not harbor more heteroplasmic mutations than controls argues that more mutations were not identified in this region in PD simply because there are more mutations everywhere. The fact that some of the specific PD associated mutations have been previously causally associated with other mitochondrial disorders suggests that they are likely to be pathogenic in PD as well. Both Taylor and Liolitsa argue that this particular region of ND5 is critical for normal catalytic function (Taylor et al., *Eur. J. Hum. Genet.* 10 (2002) 141; Liolitsa et al., *Ann. Neurol.* 53 2003 128). Furthermore, Bai et al. argue that the ND5 subunit may be controlling in complex I (Bai et al., *Moll. Cell. Biol.* 20 (2000) 805).

Two of the specific mutations identified in this study have been previously associated with other human diseases, MELAS syndrome and Leigh's syndrome. Both of these disorders are typically pediatric diseases with onset in early childhood and have no clinical similarity to Parkinson's disease. When these mutations have been associated with MELAS or Leigh's syndrome they have been present in far higher abundance.

Two competing hypotheses have been proposed to explain the presence of increased levels of mtDNA mutations in old age: accumulation of random mutations due to oxidative damage (Wallace In: *The molecular and genetic basis of neurological disease*. Rosenberg et al., editors. Boston: Buttersworths/Heinemenn (1997) 237), and differences in the expansion of inherited mutations due to genetic drift in populations of mtDNA in each cell (Parker et al., *Neurology* 44 (1994) 1086). The data presented here are compatible with either hypothesis; however, they argue against quantitative differences in the total mutation burden acquired by accelerated accumulation of random mutations as the cause of PD.

The examples below underscore the importance of using comprehensive methods of mutation analysis to find the true mutation rate. The total fraction of mutated genomes is within the range previously reported to have phenotypic results in classical single-mutation mitochondrial disorders. For example, in an LHON/MELAS overlap syndrome, the frequencies of the pathogenic mutation, G13513A, were 31% in brain, 32% in the optic nerve, and 29-70% in the muscle of affected individuals (Pulkes et al., *Ann. Neurol.* 46 (1999) 916), while in a fatal case of MELAS, this mutation was present at 25-54% frequency in a 45-year-old patient (Santorelli et al., *Biochem. Biophys. Res. Commun.* 238 (1997) 326). There are other examples of significant biochemical and pathological effects of mtDNA mutations present at the 15-45% level (Kirby et al., *Ann. Neurol.* 54 (2003) 473; Rossignol et al., *Biochem J.* 370 (2003) 751).

The mutations observed in this study could contain the substrate for complex I dysfunction in PD. Diverse mutations present within functionally important gene fragments at a low level since conception may become more prevalent by a process of clonal expansion during adult life, eventually leading to cell death. Either PD, AD, overlap syndromes or other neurodegenerative conditions may develop, depending on the most prevalent location of the mutations in each individual, and the presence of modifying nuclear or environmental factors. While no single inherited mutation causes sporadic PD, a combination of them, at levels shown in this study, could cause sufficient mitochondrial dysfunction to trigger apoptosis.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

The invention is now described with reference to the following examples. These examples are provided for the purpose of illustration only and the invention should in no way be construed as being limited to these examples, but rather should be construed to encompass any and all variations which become evident as a result of the teachings provided herein.

Example 1

High Frequency of Mitochondrial Complex I Mutations in Parkinson's Disease and Aging The present study explores the hypothesis that complex I deficiency in PD arises from the cumulative impact of multiple low abundance, heteroplasmic, amino acid-changing mutations.

Methods

DNA Preparation:

The methods described herein have been previously described elsewhere (Smigrodzki et al., *Neurobiology of Aging* 25 (2004) 1273; Parker and Parks, *Biochem. Biophys. Res. Comm.* 326 (2005) 667). We obtained mtDNA from frontal cortex rather than substantia nigra, since it manifests loss of complex I activity and because neuronal depletion in the SN in the advanced stages of PD, as found in most autopsy cases, could dilute the pathological mutations possibly present in neuronal mitochondria.

Samples were obtained from the Brain Research Facility brainbank at the University of Virginia in Charlottesville. The average age of PD samples was 77.3 years (range 72-89, S.D. 6.12 years); the average age of the aged controls was 79.7 years (range 72-84, S.D. 4.23 years). The PD or control status of each sample was verified by medical history and autopsy. Controls had no clinical or autopsy findings of any neurodegenerative disorder. Equivalent pieces of frontal cortex were obtained in each case. Total genomic DNA was purified from fresh-frozen autopsy samples of frontal cortex using the QiaAmp kit (Qiagen). The concentration and purity of all DNA extracts was checked spectrophotometrically before storage at a concentration of 10 ng/μl at −80° C.

PCR Amplification:

Fragments of mtDNA covering complex I genes were amplified with HotStart Pfu DNA polymerase (Stratagene) following manufacturer's instructions for enzyme, dNTP and primer concentrations. The listing of primer pairs is given in Table 1. The PCR program was: 2 min at 94° C., followed by 25 cycles of denaturation at 94° C. for 15 s, annealing at 55.5°C. (or 53.5° C. for the D3 primer pair) for 30 s, extension at 72° C. for 1 min, followed by a final extension step at 72° C. for 7 min. The amplifications were performed in 100-$^{82}$ μl volumes using 100 ng of template DNA. The size and quality of PCR products were verified on an agarosegel. Negative controls were included in all reaction batches, and no false-positive products were observed. The number of PCR cycles was optimized at 25 to avoid overamplification, which may result in artifacts. To test for amplification of pseudogene sequences, PCR reactions under the above conditions were run with 100 ng of ρ° cell total DNA. The primer pairs B2, D3, D4, and D5 produced very faint bands, about 1% of the intensity seen with a control DNA template, other pairs did not amplify any products.

TABLE 1

PCR primers

| Name | Sequence | Direction | Position |
|---|---|---|---|
| SEQ ID NO.: 1 | CCGTACAACCCTAACATAACCA | Forward | 5052-5955 |
| SEQ ID NO.: 2 | GTGTTCCAATGTCTTTGTGGTT | Reverse | 5052-5955 |
| SEQ ID NO.: 3 | TCTCAGCCCTCCTAATGACCTC | Forward | 9271-10153 |
| SEQ ID NO.: 4 | TCTATGTAGCCGTTGAGTTGTG | Reverse | 9271-10153 |
| SEQ ID NO.: 5 | CAACACCCTCCTAGCCCTACTAC | Forward | 10085-10975 |
| SEQ ID NO.: 6 | GAGTCAGGTAGTTAGTATTAGGAG | Reverse | 10085-10975 |
| SEQ ID NO.: 7 | CTGTTCCCCAACCTTTTCCT | Forward | 10912-11861 |
| SEQ ID NO.: 8 | CGAGGTTAGCGAGGCTTG | Reverse | 10912-11861 |
| SEQ ID NO.: 9 | GCACTCACAGTCGCATCATAAT | Forward | 11766-12684 |
| SEQ ID NO.: 10 | CTGATTAATGTTTGGGTCTGAG | Reverse | 11766-12684 |
| SEQ ID NO.: 11 | CCCTGTAGCATTGTTCGTT | Forward | 12606-13559 |
| SEQ ID NO.: 12 | GCTCAGGCGTTTGTGTATG | Reverse | 12606-13559 |
| SEQ ID NO.: 13 | CAGGAATACCTTTCCTCACAGG | Forward | 13478-13992 |
| SEQ ID NO.: 14 | GAGGAGTAGGGGCAGGTTTT | Reverse | 13478-13992 |
| SEQ ID NO.: 15 | AAATCCCCACTATGCACATTTT | Forward | 13876-14342 |
| SEQ ID NO.: 16 | GGGTGGTGGTTGTGGTAAAC | Reverse | 13876-14342 |
| SEQ ID NO.: 17 | CCCCGAGCAATCTCAATTAC | Forward | 14156-14613 |
| SEQ ID NO.: 18 | TCTAAGCCTTCTCCTATTTATGG | Reverse | 14156-14613 |
| SEQ ID NO.: 19 | CCGCTAACAATCAATACTAAACC | Forward | 14567-15516 |
| SEQ ID NO.: 20 | GTATAATTGTCTGGGTCGCCTA | Reverse | 14567-15516 |
| SEQ ID NO.: 21 | TCCGAGCAGTACATGCTAAG | Forward | 2841-3361 |
| SEQ ID NO.: 22 | ATGCCATTGCGATTAGAATG | Reverse | 2841-3361 |
| SEQ ID NO.: 23 | CAACCTCCTACTCCTCATTGTAC | Forward | 3318-4235 |
| SEQ ID NO.: 24 | GTAATGGGTATGGAGACATATC | Reverse | 3318-4235 |
| SEQ ID NO.: 25 | AACTTCCTACCACTCACCCTAG | Forward | 4180-5121 |
| SEQ ID NO.: 26 | GTAGGAATGCGGTAGTAGTTAG | Reverse | 4180-5121 |

Cloning and Sequencing of PCR Products:

PCR product remaining after minigel verification (95 µl) was purified with the Qiaquick kit (Qiagen), mixed with a loading buffer containing 0.2% of crystal violet, and run on a 1% agarose gel stained with 0.0001% crystal violet. DNA bands were excised and recovered from gel slices with the Qiaquick Gel Extraction Kit (Qiagen). Crystal violet was used to visualize DNA bands rather than ethidium bromide in order to minimize UV damage to DNA during preparation. The concentration and purity of DNA was verified spectrophotometrically. Freshly purified PCR products were ligated to the pCR 4Blunt-TOPO vector (Zero Blunt PCR Cloning Kit for Sequencing, Invitrogen) and used to transform TOP10 Chemically Competent cells, according to manufacturer's instructions. Cells were plated on carbenicillin LB agar plates, and grown for 24-30 h at 30° C. For each PCR product, 96 colonies were picked into 96-well blocks (Qiagen) with Terrific Broth (Sigma) and carbenicillin, and grown with shaking at 30° C. for 30-36 h. Plasmid DNA was purified using the Qiaquick Miniprep Kit (Qiagen) on a BioRobot 9600 (Qiagen), according to manufacturer's protocol. Concentration of the DNA was adjusted to 50 ng/µl, and 7 µl were used in sequencing reactions using the PCR Cycle Sequencing Kit (Amersham), as per manufacturer's instructions, at half-strength reaction mix concentration. Excess dyes were removed with AutoSeq plates (Amersham) and run on an Applied Biosystems ABI-Prism 3700 DNA Analyzer. Plates that were to be loaded after more than 3 h were vacuum dried and re-suspended in Megabace Loading Solution (Amersham).

Data Analysis:

The raw sequencer output was analyzed with the Phred base-calling software (CodonCode), and transferred for further processing to the Sequencher sequence analysis suite (Gene Codes Corporation). Sequences were assembled and compared to the amended Cambridge human consensus mtDNA sequence. All mutations were verified by visual inspection of the chromatograms. Only unequivocally mutated bases were included in the mutation database. Clones with more than two mutations or with large rearrangements were excluded from the analysis, because of the possibility of derivation from nuclear pseudogenes. The total number of clones in the entire study rejected on this basis was approximately 30, and they did not preferentially occur in the fragments that had a weak ability to amplify DNA out of $\rho^\circ$ template.

Statistical analysis included repeated measures ANOVA and ANOVA on ranks. Generalized estimating equations as implemented in SAS as PROC GENMOD, were also used, controlling for the repeated measures for the multiple clones derived from each individual and for the repeated measures for the multiple genes sequenced for each clone. Thus the analysis was able to accommodate the "double clustering" of the study design.

Additional analysis of the data was performed using a genetic algorithm approach, combined with an evolutionary conservation profile (Ng and Henikoff *Nucl. Acids Res.* 31(2003) 3812) and an amino acid dissimilarity index (Xia and Xie, *Mol. Biol. Evol.* 19 (2002) 58). Briefly, the mutations were scored according to their location within genes and the type of amino acid substitutions. The modified scores were used as in input for a genetic algorithm that identified areas within each gene correlating with PD status and produced classifying functions for differentiating PD versus control. The validity of the functions was analyzed by running the whole computation on subsets of patients (of 11 patients each) and using the resulting classifying function to classify the remaining patient (the "leave-one-out" tests) (not shown).

Results

A total of 15 299 clones was analyzed, representing an average 94.4-fold coverage of complex I in six PD and six controls. The total number of bases sequenced was $7.19 \times 10^6$, spanning all seven mitochondrial complex I genes. Table 2 lists number, type, and frequency of the mutations detected. Most clones had only one mutation, with approximately 10% of the mutated clones having 2 mutations. A total of 68 homoplasmic mutations and high-level heteroplasmic mutations corresponding to known polymorphisms were also observed (data not shown). Additionally, some data was collected for the tRNA genes (MTTE, MTTG, MTTI, MTTL2, MTTM, MTTR, MTTQ), parts of cytochrome B and D-loop sections located in the vicinity of complex I genes, with a total of $1.32 \times 10^6$ additional bases sequenced. No mutation hotspots were observed.

TABLE 2

List of mutations in complex I genes

| | Gene and mutation type | | | | | | | | | | | |
|---|---|---|---|---|---|---|---|---|---|---|---|---|
| | ND1 (Fs[a]) | ND1 (Aa[b]) | ND1 (S[c]) | ND2 (FS) | ND2 (AA) | ND2 (S) | ND3 (FS) | ND3 (AA) | ND3 (S) | ND4L (FS) | ND4L (AA) | ND4L (S) |
| Control | | | | | | | | | | | | |
| 8 | 1 | 1 | 1 | 0 | 0 | 0 | 2 | 0 | 0 | 1 | 0 | 0 |
| 11 | 2 | 7 | 3 | 1 | 7 | 2 | 0 | 0 | 1 | 0 | 2 | 2 |
| 12 | 0 | 1 | 1 | 1 | 3 | 0 | 0 | 1 | 0 | 0 | 0 | 0 |
| 15 | 1 | 12 | 0 | 0 | 17 | 3 | 0 | 5 | 2 | 0 | 1 | 0 |
| 16 | 4 | 16 | 1 | 7 | 7 | 1 | 0 | 2 | 0 | 0 | 1 | 1 |
| 17 | 2 | 9 | 2 | 1 | 7 | 3 | 1 | 1 | 1 | 1 | 1 | 0 |
| Total PD | | | | | | | | | | | | |
| 6 | 1 | 14 | 6 | 5 | 15 | 7 | 0 | 1 | 0 | 1 | 1 | 0 |
| 9 | 1 | 7 | 1 | 1 | 3 | 0 | 0 | 2 | 0 | 0 | 3 | 1 |
| 10 | 5 | 7 | 7 | 2 | 15 | 5 | 0 | 1 | 0 | 0 | 3 | 1 |
| 13 | 0 | 2 | 3 | 0 | 3 | 0 | 1 | 2 | 1 | 0 | 2 | 0 |
| 14 | 1 | 5 | 1 | 2 | 9 | 1 | 1 | 2 | 0 | 0 | 1 | 0 |
| 18 | 1 | 5 | 1 | 2 | 4 | 0 | 1 | 0 | 0 | 0 | 1 | 0 |
| Total | | | | | | | | | | | | |
| Total FS | 19 | | | 22 | | | 6 | | | 3 | | |
| Total AA | | 86 | | | 89 | | | 17 | | | 16 | |
| Total S | | | 26 | | | 22 | | | 5 | | | 5 |
| All mutations | | | | | | | | | | | | |

| | Gene and mutation type | | | | | | | | | |
|---|---|---|---|---|---|---|---|---|---|---|
| | ND4 (FS) | ND4 (AA) | ND4 (S) | ND5 (FS) | ND5 (AA) | ND5 (S) | ND6 (FS) | ND6 (AA) | ND6 (S) | Total |
| Control | | | | | | | | | | |
| 8 | 3 | 7 | 6 | 0 | 9 | 2 | 1 | 0 | 0 | 34 |
| 11 | 1 | 5 | 2 | 2 | 16 | 8 | 0 | 1 | 0 | 62 |
| 12 | 0 | 3 | 1 | 1 | 1 | 1 | 0 | 2 | 0 | 15 |
| 15 | 1 | 7 | 0 | 3 | 4 | 1 | 5 | 7 | 3 | 72 |

TABLE 2-continued

List of mutations in complex I genes

| | | | | | | | | | | |
|---|---|---|---|---|---|---|---|---|---|---|
| 16 | 2 | 4 | 0 | 2 | 10 | 6 | 2 | 1 | 1 | 68 |
| 17 | 2 | 5 | 2 | 1 | 13 | 1 | 1 | 4 | 0 | 58 |
| Total PD | | | | | | | | | | 309 |
| 6 | 4 | 2 | 0 | 10 | 15 | 7 | 0 | 4 | 0 | 93 |
| 9 | 2 | 7 | 1 | 1 | 10 | 4 | 0 | 3 | 0 | 47 |
| 10 | 6 | 13 | 4 | 3 | 11 | 6 | 2 | 0 | 0 | 91 |
| 13 | 1 | 0 | 1 | 3 | 2 | 5 | 0 | 1 | 0 | 26 |
| 14 | 3 | 4 | 0 | 3 | 10 | 1 | 2 | 5 | 2 | 53 |
| 18 | 0 | 11 | 1 | 1 | 6 | 3 | 0 | 0 | 0 | 37 |
| Total | | | | | | | | | | 347 |
| Total FS | 25 | | | 30 | | | 13 | | | 118 |
| Total AA | | 68 | | | 107 | | | 28 | | 411 |
| Total S | | | 18 | | | 45 | | | 6 | 127 |
| All mutations | | | | | | | | | | 656 |

[a]Frameshift mutations
[b]Aminoacid-changing mutations
[c]Silent mutations

Correction for PCR error rate <k> was calculated as described by Simon and co-workers (Lin et al., *Hum. Mol. Genet.* 11 (2002), 133), using the $1.3 \times 10^{-6}$ base error rate (f) of the Pfu polymerase, a length of 900 bp for the PCR product (L), 0.985 as fraction of amplified strands per cycle (η) and 25 cycles of PCR (c) in the formula $<k>|L = cf\eta/1+\eta$. Our estimated error rate ($<k>|L$) is $16.1 \times 10^{-6}$ bp. Additionally, we performed an amplification from 1 ng of a B2-fragment clone from our collection (roughly equivalent in terms of target sequence copy number to 100 ng of genomic DNA template), subjected the products to the same cloning and sequencing procedure as used for samples, and found two errors in 141 000 bp, corresponding to a mutation rate of $14.2 \times 10^{-6}$ bp.

There was no significant difference in total mutation burden between PD and aged control samples. The average amino acid-changing mutation frequencies (after applying the PCR error correction) were 59.3 per million basepairs in complex I genes, 66.1 per million in cytochrome B and tRNA genes, and 640 mutations per million in the D-loop. Known polymorphisms and high-level heteroplasmic mutations are not included in this average. Assuming random distribution of amino acid-changing complex I mutations, the total percentage of genomes with a mutated complex I gene would be 32%.

The percentages of mutations at the first, second and third codon positions were 30.5, 32.8 and 36.1, respectively. The percentages of transitions were 39% in the PD group, and 29% in the control group, transversions were 42% in PD and 54% in controls, and frameshifts were 18 and 16%, respectively. These differences are not statistically significant.

The genetic algorithm analysis derived a group of classifying functions capable of differentiating PD versus control patients with 100% accuracy. On all 12 leave-one-out tests the classifying function correctly classified the left-out patient. The functions highlighted for example areas of ND2, and ND5 as having a higher mutation load in PD patients than in controls (Table 3).

TABLE 3

Locations with mutations predominantly in PD patients

| | Gene and location | | | | |
|---|---|---|---|---|---|
| | ND2, 4470–4500 | ND2, 4934–5048 | ND2, 5281–5395 | ND5, 12680–12790 | ND5, 13330–13460 |
| Control | | | | | |
| 8 | | | | | |
| 11 | | | | | |
| 12 | | | | | |
| 15 | | | | * | |
| 16 | | | | | |
| 17 | | | * | | |
| PD | | | | | |
| 6 | * | *** | *** | *** | |
| 9 | * | | | *** | * |
| 10 | * | ** | | * | ** |

TABLE 3-continued

Locations with mutations predominantly in PD patients

Gene and location

| | ND2, 4470–4500 | ND2, 4934–5048 | ND2, 5281–5395 | ND5, 12680–12790 | ND5, 13330–13460 |
|---|---|---|---|---|---|
| 13 | * | | | * | |
| 14 | | | * | *** | ** |

Asterisk denotes amino acid-changing mutation.

Several amino acid-changing mutations were identified in multiple PD brains but in no control brains (examples given in Table 4). Of particular interest are the changes in codon 145 of ND5 where mutations were observed in three of the six PD brains. This mutation is of known pathogenic significance having been observed in MELAS.

TABLE 4

Amino acid-changing mutations seen in multiple PD brains and no controls
(percentages of mutated clones in each patient given with the amino acid change)

Gene

| Patient | ND2, codon 5 | ND2, codon 187 | ND2, codon 239 | ND4L, codon 77 | ND5, codon 145 |
|---|---|---|---|---|---|
| 6 | | | | L-F, 1.18% | |
| 9 | A-T, 1.25% | | | | E-G, 1.39% |
| 10 | | M-T, 6.25% | | L-F, 1.18% | |
| 13 | A-V, 1.12% | | | | E-V, 1.09% |
| 14 | | | I-M, 1.2% | | E-D, 1.35% |
| 18 | | M-I, 1.33% | I-H, 1.33% | | |

Example 2

Mitochondrial ND5 Mutations in Idiopathic Parkinson's Disease: Identity and Frequency of Amino Acid Changing Mutations in the Selected Region of ND5

The present study was performed to evaluate this observation prospectively and to test the hypothesis that the presence or absence of amino acid changing mutations in this region of ND5 correlate with PD. To investigate the predictive potential of the observation, we analyzed the amino acid changing mutations in sixteen brain samples. Eight samples were obtained form PD patients and the other eight samples were from control patients. s. The data demonstrate that the presence or absence of amino acid changing heteroplasmic mutations in this region was correctly classified in 15 out of 16 brain samples (Parker and Parks, *Biochem. Biophys. Res. Com.* 326 (2005) 667). The only false positive was a control patient, 78 years of age who had not been diagnosed with PD.

Methods:

Methods employed in this study were similar to Example 1: Genomic DNA was extracted from frontal lobe tissue from 8 idiopathic PD samples and 8 similarly aged controls (PD mean age, 78; control mean age, 74;). The region of interest in ND5 was PCR amplified and 96 independent clones from each sample were then cycle sequenced. Sequencer data were aligned against the wildtype sequence (Sequencher, Gene Codes) and all potential mutations were operator verified. Usable sequence data were obtained on an average of 84 independent clones for PD samples and 91 independent clones for control samples.

Results

Results of the present study are summarized and compared with the results of Example 1 (see Table 5). Fifteen of 16 samples studied were correctly identified as either PD or control on the basis of the presence or absence of amino acid changing mutations in the specific regions studied. A single control was misidentified as PD. Whether or not this individual would have developed Parkinson's disease later in life is unknowable. As in Example 1 we identified a specific mutation that has been causally associated in much higher abundance with an earlier onset neurodegenerative disorders: Leigh's disease (codon 124; F to L) (Taylor et al., *Eur. J. Hum. Genet.* 10 (2002), 141; Lebon et al., *J. Med. Genet.* 40 (2003) 896; Liolitsa et al., *Ann. Neurol.* 53 (2003), 128). In addition, several PD samples had other significant but not previously described changes at codon 145.

TABLE 5

Identity and frequency of amino acid changing mutations
in the selected region of ND5
Individual brain samples

| Example 2 (codon, change, %) | | Example 1 (codon, change, %) | |
|---|---|---|---|
| PD (n = 8) | Control (n = 8) | PD (n = 6) | Control (n = 6) |
| 124, F-L, 8.4% | 134, A-T, 1.12% | 130, I-L, 5.71% | |
| 143, G-A, 1.04% | | 134, A-G, 4.21% | |
| | | 145, E-D, 1.35% | |
| 136, N-Y, 1.08% | | 133, T-A, 1.52% | |
| 136, N-S, 1.16% | | 136, N-D, 1.15% | |
| | | 145, E-G*, 1.39% | |
| 138, F-S, 0.97% | | 148, G-W, 0.67% | |
| 141, F-S, 0.97% | | 145, E-V, 1.09% | |

TABLE 5-continued

Identity and frequency of amino acid changing mutations
in the selected region of ND5
Individual brain samples

| Example 2 (codon, change, %) | | Example 1 (codon, change, %) | |
|---|---|---|---|
| PD (n = 8) | Control (n = 8) | PD (n = 6) | Control (n = 6) |
| 145, E-ter, 1.19% | | | |
| 148, G-ter, 1.0% | | | |
| 148, G-ter, 0.94% | | | |

Mutations known to be associated with other neurologic diseases are designated*.

Mutations known to be associated with other neurologic diseases are designated*.

Although outside of the region under investigation in this study, it is noted that some PD samples had amino acid changing mutations at codon 236 and at codon 250. Codon 237 has been associated with an illness combining features of MELAS, Leber's hereditary optic neuropathy, and Leigh's disease (Liolitsa et al., *Ann. Neurol.* 53 (2003) 128). Mutation at codon 250 has been associated with MELAS/Leigh's disease (Crimi et al., *Neurology* 60 (2003), 1857).

A similar methodology was used on blood obtained from a PD patient. Analysis of the mutations showed low frequency heteroplasmic amino acid changing mutations at codons 136, 142, 145, 148 and 155. This experiment on platelet cells showed that the methodology developed with brain samples can be expanded to other sources of mtNDA.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Accordingly, the present invention is not intended to be limited to the embodiments shown herein, but is to be accorded the widest scope consistent with the principles and novel features disclosed herein.

I claim:

1. A method of diagnosing if a human subject has or will develop Parkinson's Disease, comprising
    determining the presence or absence in the subject of a heteroplasmic, amino acid changing mutation in a region of the mitochondrial ND5 gene,
    wherein the region comprises codons 124-148,
    wherein the presence of the heteroplasmic, amino acid changing mutation at one or more of codons 124-148 of the mitochondrial ND5 gene indicates that the human subject has or will develop Parkinson's Disease.

2. The method of claim 1, wherein the region comprises codons 130-148.

3. The method of claim 2, wherein the region comprises codons 136-148.

4. The method of claim 1, wherein the region comprises codon 145.

5. The method of claim 1, wherein the heteroplasmic mutation involves at least one of codons 124, 130, 133, 134, 136, 138, 141, 142, 143, 145, and 148.

6. The method of claim 1, wherein the heteroplasmic mutation comprises at least one of the following codon mutations:
    124, F-L
    130, I-L
    133, T-A
    134, A-G
    136, N-Y
    136, N-S
    136, N-D
    138, F-S
    141, F-S
    143, G-A
    145, E-D
    145, E-G
    145, E-V
    145, E-ter
    148, G-W or
    148, G-ter.

7. The method of claim 1, wherein the method confirms a clinical diagnosis of Parkinson's Disease.

8. A method of diagnosing if a human subject has Parkinson's Disease, comprising
    determining the presence or absence in the subject of a heteroplasmic, amino acid changing mutation in a region of the mitochondrial ND5 gene,
    wherein the region comprises codons 124-148,
    wherein the presence of the heteroplasmic, amino acid changing mutation at one or more of codons 124-148 of the mitochondrial ND5 indicates that the human subject has Parkinson's Disease.

* * * * *

UNITED STATES PATENT AND TRADEMARK OFFICE
CERTIFICATE OF CORRECTION

| | | |
|---|---|---|
| PATENT NO. | : 7,537,893 B2 | Page 1 of 1 |
| APPLICATION NO. | : 11/363531 | |
| DATED | : May 26, 2009 | |
| INVENTOR(S) | : W. David Parker, Jr. | |

It is certified that error appears in the above-identified patent and that said Letters Patent is hereby corrected as shown below:

Column 1, line 15-16, delete "The United States Government may have certain rights in the invention.", and insert --The United States Government has certain rights in the invention.--

Signed and Sealed this

Nineteenth Day of October, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,537,893 B2 | Page 1 of 1 |
| APPLICATION NO. | : 11/363531 | |
| DATED | : May 26, 2009 | |
| INVENTOR(S) | : W. Davis Parker, Jr. | |

It is certified that error appears in the above-identified patent and that said Letters Patent is hereby corrected as shown below:

Claim 1, line 7 (column 29, line 37) delete "the" after "of" and substitute --a--.
It should read as shown below:

--wherein the presence of a heteroplasmic, amino acid--

Claim 8, line 7 (column 30, line 51) delete "the" after "of" and substitute --a--.
It should read as shown below:

--wherein the presence of a heteroplasmic, amino acid--

Claim 8, line 9 (column 30, line 53) insert --gene-- after "ND5".
It should read as shown below:

--the mitochondrial ND5 gene indicates that the human subject--

Signed and Sealed this
Twenty-fifth Day of January, 2011

David J. Kappos
*Director of the United States Patent and Trademark Office*